United States Patent
Fukui et al.

(10) Patent No.: US 6,709,833 B2
(45) Date of Patent: *Mar. 23, 2004

(54) MONOCLONAL ANTIBODY RECOGNIZING PHOSPHATIDYLINOSITOL-3,4-DIPHOSPHATE

(75) Inventors: Yasuhisa Fukui, Musashino (JP); Satoshi Nagata, Rockville, MD (US); Ryuichi Shirai, Ikoma (JP); Naoaki Saito, Kobe (JP)

(73) Assignees: Yasuhisa Fukui, Tokyo (JP); Medical & Biological Laboratories, Co., Ltd., Aichi (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/518,737

(22) Filed: Mar. 3, 2000

(65) Prior Publication Data

US 2003/0008321 A1 Jan. 9, 2003

(30) Foreign Application Priority Data

Sep. 3, 1999 (JP) .......................... 11/250209

(51) Int. Cl.[7] .................. C07K 16/28; C12P 21/08; G01N 33/53; G01N 33/554; G01N 33/577
(52) U.S. Cl. .................. 435/7.95; 435/7.21; 435/7.23; 435/7.92; 435/70.21; 435/452; 435/326; 435/343; 435/975; 436/519; 436/548; 436/71; 530/387.3; 530/388.2; 530/388.7; 530/389.6
(58) Field of Search .................. 435/7.92, 15, 70.21, 435/452, 326, 343, 975, 7.95, 7.21, 7.23; 436/547, 548, 519, 71; 530/388.1, 388.2, 388.7, 389.1, 389.6, 387.3

(56) References Cited

PUBLICATIONS

Yokogawa et al., 2000. Evidence that . . . with monoclonal antibodies specific for PI 3,4–P2. FEBS Lett. 473: 222–226.*
Fukami et al., Proc. Natl. Acad. Sci. U.S.A., 85:9057–9061 (1988).
Matuoka et al., Science, 239:640–643 (1988).
Boronenkov et al., Mol. Biol. Cell, 9:3547–3560 (1998).
Coffer et al. Biochem, J., 335:1–13 (1998).
Galanos et al., Eur. J. Biochem., 24:116–122 (1971).
Miyazawa et al., Mol. Immunol., 25:1025–1031 (1988).
Rameh et al., J. Biol. Chem., 274:8347–8350 (1999).
Sawada et al., Chem. Pharm. Bull., 45:1521–1523 (1997).
Shirai et al., Tetrahedron Lett., 39; 9485–9488 (1998).
Shirai et al., Tetrahedron Lett., 40: 1693–1696 (1999).
Thum et al., Tetrahedron Lett., 37:9017–9020 (1996).
Umeda et al., J. Immun., 137:3264–3269 (1986).
Umeda et al., J. Immun., 136:2562–2567 (1986).

* cited by examiner

Primary Examiner—Christopher L. Chin
Assistant Examiner—James L. Grun
(74) Attorney, Agent, or Firm—Peter F. Corless; Christine C. O'Day; Edwards & Angell, LLP

(57) ABSTRACT

A novel monoclonal antibody that specifically recognizes phosphatidylinositol-3,4-biphosphate (PI-3,4-P2) but does not cross-react with structurally similar phospholipid antigens is advantageous for PI-3,4-P2-specific immunoassay. The gene in the variable regions of the monoclonal antibody has been identified, which enables producing recombinant antibodies.

5 Claims, 10 Drawing Sheets

AMINO ACID SEQUENCE OF 8C2 VARIABLE REGIONS

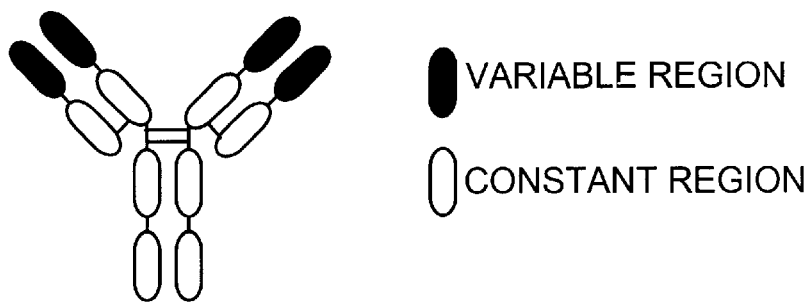

LIGHT CHAIN VARIABLE REGION

DVVMTQTPLSLPVSLGDQASISC[RSSQSLVHSNGNTYLH] ←CDR L1

WYLQKPGQSPKLLIY[KVSNRFS]GVPDRFSGSGTRTDFTL ←CDR L2

KISRVEAEDLGVYFC[SQSTHVPYT]FGGGTKLEIK ←CDR L3

HEAVY CHAIN VARIABLE REGION

EVQLVESGGDLVKPGGSVKLSCAAS[GFTFSSY]GMSWAR ←CDR H1

QTPDKRLEWVASI[SSGGSY]TYYPDSVKGRFTISRDNAKN ←CDR H2

TLYLQMSSLKSEDTAMYYCAR[QRGYVNFGIAY]WGQGT ←CDR H3

LVTVSAATTT

FIG. 6

Wortmanin (−)
Phase contrast
FIG. 7A  FIG. 7B  FIG. 7C
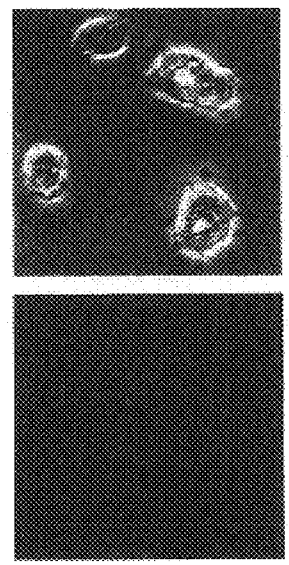 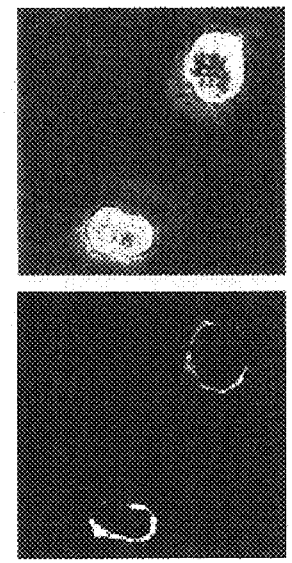 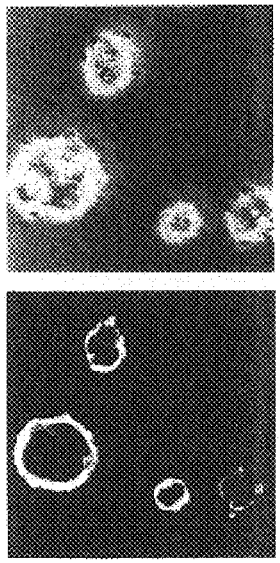
Fluorescent
FIG. 7D  FIG. 7E  FIG. 7F Wortmanin (+)
FIG. 7G  FIG. 7H  FIG. 7I
Phase contrast
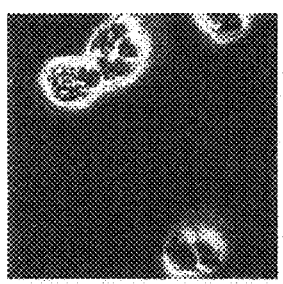 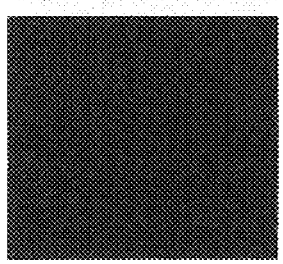 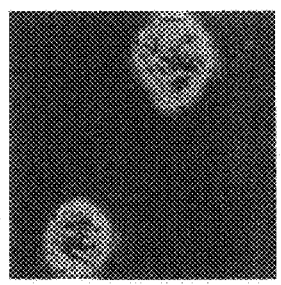
Fluorescent
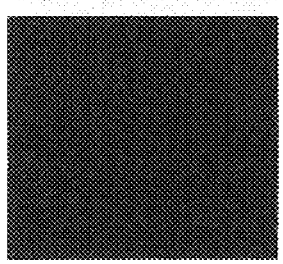 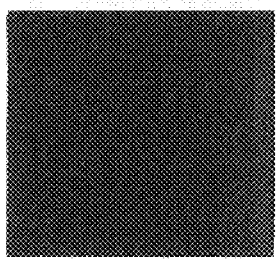
FIG. 7J  FIG. 7K  FIG. 7L Fluorescent        Phase contrast
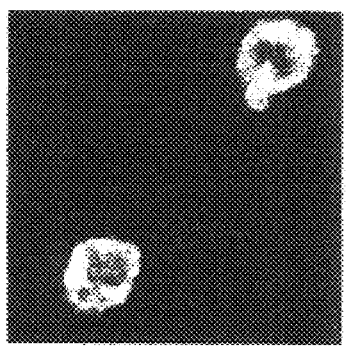 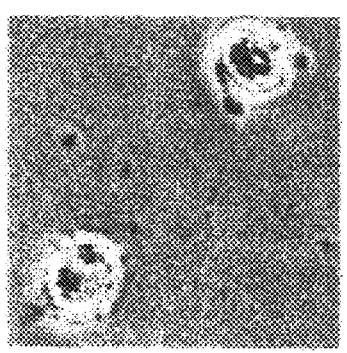
No Competitor
FIG. 8A              FIG. 8B
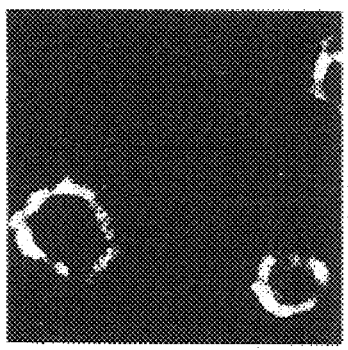 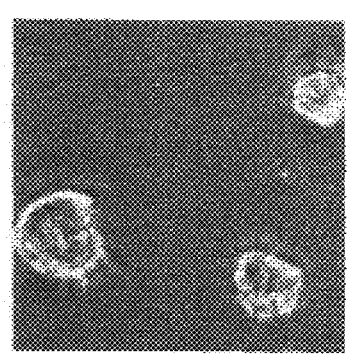
PC
50 μM
FIG. 8C              FIG. 8D
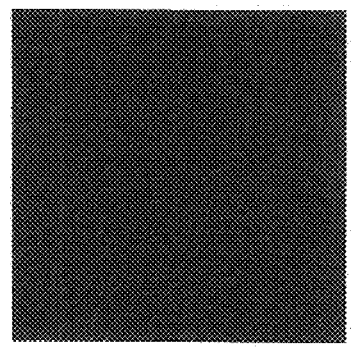 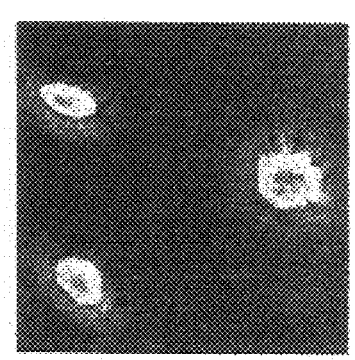
PC-3,4-P2
50 μM
FIG. 8E              FIG. 8F
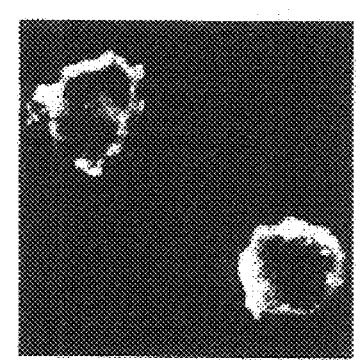 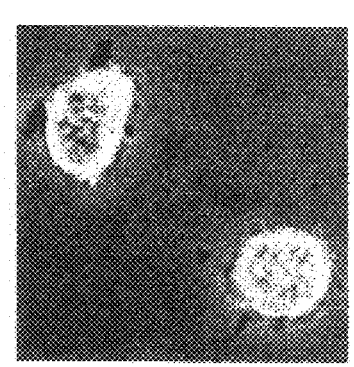
PC-4,5-P2
50 μM
FIG. 8G              FIG. 8H

SEQUENCE LISTING

<160> NUMBER OF SEQ ID NOS: 10

<210> SEQ ID NO 1
<211> LENGTH: 372
<212> TYPE: DNA
<213> ORGANISM: Mus musculus
<220> FEATURE:
<221> NAME/KEY: CDS
<222> LOCATION: (1)..(372)

<400> SEQUENCE: 1

```
gag gtg caa ctg gtg gag tct ggg gga gac tta gtg aaa cct gga ggg      48
Glu Val Gln Leu Val Glu Ser Gly Gly Asp Leu Val Lys Pro Gly Gly
 1               5                  10                  15 tcc gtg aaa ctc tcc tgt gca gcc tct gga ttc act ttc agt agc tat      96
Ser Val Lys Leu Ser Cys Ala Ala Ser Gly Phe Thr Phe Ser Ser Tyr
                20                  25                  30 ggc atg tct tgg gct cgc cag act cca gac aag agg ctg gag tgg gtc     144
Gly Met Ser Trp Ala Arg Gln Thr Pro Asp Lys Arg Leu Glu Trp Val
            35                  40                  45
```

```
gca agc att agt agt ggt ggt agt tac acc tac tat cca gac agt gtg      192
Ala Ser Ile Ser Ser Gly Gly Ser Tyr Thr Tyr Tyr Pro Asp Ser Val
         50                  55                  60 aag ggg cga ttc acc atc tcc aga gac aat gcc aag aac acc ctg tac      240
Lys Gly Arg Phe Thr Ile Ser Arg Asp Asn Ala Lys Asn Thr Leu Tyr
 65                  70                  75                  80 ctg caa atg agc agt ctg aag tct gag gac aca gcc atg tac tac tgt      288
Leu Gln Met Ser Ser Leu Lys Ser Glu Asp Thr Ala Met Tyr Tyr Cys
                 85                  90                  95 gca aga cag agg ggc tat gtt aac ttc ggg att gct tac tgg ggc caa      336
Ala Arg Gln Arg Gly Tyr Val Asn Phe Gly Ile Ala Tyr Trp Gly Gln
             100                 105                 110 ggg act ctg gtc act gtc tct gca gct aca aca aca                      372
Gly Thr Leu Val Thr Val Ser Ala Ala Thr Thr Thr
         115                 120

<210> SEQ ID NO 2
<211> LENGTH: 124
<212> TYPE: PRT
<213> ORGANISM: Mus musculus

<400> SEQUENCE: 2

Glu Val Gln Leu Val Glu Ser Gly Gly Asp Leu Val Lys Pro Gly Gly
 1               5                  10                  15

Ser Val Lys Leu Ser Cys Ala Ala Ser Gly Phe Thr Phe Ser Ser Tyr
             20                  25                  30

Gly Met Ser Trp Ala Arg Gln Thr Pro Asp Lys Arg Leu Glu Trp Val
         35                  40                  45

Ala Ser Ile Ser Ser Gly Gly Ser Tyr Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Gln Arg Gly Tyr Val Asn Phe Gly Ile Ala Tyr Trp Gly Gln
            100                 105                 110

Gly Thr Leu Val Thr Val Ser Ala Ala Thr Thr Thr
        115                 120

<210> SEQ ID NO 3
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 3 gat gtt gtg atg acc caa act cca ctc tcc ctg cct gtc agt ctt gga      48
Asp Val Val Met Thr Gln Thr Pro Leu Ser Leu Pro Val Ser Leu Gly
 1               5                  10                  15 gat cag gcc tcc atc tct tgc aga tct agt cag agc ctt gta cac agt      96
Asp Gln Ala Ser Ile Ser Cys Arg Ser Ser Gln Ser Leu Val His Ser
             20                  25                  30 aat gga aac acc tat tta cat tgg tac ctc cag aaa cca ggc cag tct      144
Asn Gly Asn Thr Tyr Leu His Trp Tyr Leu Gln Lys Pro Gly Gln Ser
         35                  40                  45 cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
     50                  55                  60
```

```
gac agg ttc agt ggc agt gga aca agg aca gat ttc aca ctc aag atc      240
Asp Arg Phe Ser Gly Ser Gly Thr Arg Thr Asp Phe Thr Leu Lys Ile
 65                  70                  75                  80 agc aga gtg gag gct gag gat ctg gga gtt tat ttc tgc tct caa agt      288
Ser Arg Val Glu Ala Glu Asp Leu Gly Val Tyr Phe Cys Ser Gln Ser
                 85                  90                  95 aca cat gtt ccg tac acg ttc gga ggg ggg acc aag ctg gaa ata aaa      336
Thr His Val Pro Tyr Thr Phe Gly Gly Gly Thr Lys Leu Glu Ile Lys
            100                 105                 110
```

<210> SEQ ID NO 4
<211> LENGTH: 112
<212> TYPE: PRT
<213> ORGANISM: Mus musculus

<400> SEQUENCE: 4

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Thr Arg Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Tyr Thr Phe Gly Gly Gly Thr Lys Leu Glu Ile Lys
            100                 105                 110
```

<210> SEQ ID NO 5
<211> LENGTH: 7
<212> TYPE: PRT
<213> ORGANISM: Mus musculus

<400> SEQUENCE: 5

```
Gly Phe Thr Phe Ser Ser Tyr
 1               5
```

<210> SEQ ID NO 6
<211> LENGTH: 6
<212> TYPE: PRT
<213> ORGANISM: Mus musculus

<400> SEQUENCE: 6

```
Ser Ser Gly Gly Ser Tyr
 1               5
```

<210> SEQ ID NO 7
<211> LENGTH: 11
<212> TYPE: PRT
<213> ORGANISM: Mus musculus

<400> SEQUENCE: 7

```
Gln Arg Gly Tyr Val Asn Phe Gly Ile Ala Tyr
 1               5                  10
```

<210> SEQ ID NO 8
<211> LENGTH: 16
<212> TYPE: PRT

```
<213> ORGANISM: Mus musculus

<400> SEQUENCE: 8

Arg Ser Ser Gln Ser Leu Val His Ser Asn Gly Asn Thr Tyr Leu His
  1               5                  10                  15

<210> SEQ ID NO 9
<211> LENGTH: 7
<212> TYPE: PRT
<213> ORGANISM: Mus musculus

<400> SEQUENCE: 9

Lys Val Ser Asn Arg Phe Ser
  1               5

<210> SEQ ID NO 10
<211> LENGTH: 9
<212> TYPE: PRT
<213> ORGANISM: Mus musculus

<400> SEQUENCE: 10

Ser Gln Ser Thr His Val Pro Tyr Thr
  1               5
```

MONOCLONAL ANTIBODY RECOGNIZING PHOSPHATIDYLINOSITOL-3,4-DIPHOSPHATE

FIELD OF THE INVENTION

The present invention relates to a monoclonal antibody to phosphatidylinositol-3,4-diphosphate and a method for immunoassay using the monoclonal antibody.

BACKGROUND OF THE INVENTION

Formerly, phospholipids in living organisms was merely appreciated as constituents of cell membranes. Recently, however, inositol phospholipid, a member of phospholipids, has been found to play an important role in the intracellular signal transduction system. In particular, metabolism of phosphatidylinositol (PI), a phospholipid present in biomembranes, has been extensively investigated because abnormality of this system is known to induce aberrant cell proliferation and causes cancers.

It was commonly believed that inositol phospholipids are synthesized as follows: the 4-position of PI is phosphorylated by the action of phosphatidylinositol-4-kinase (PI4K) to generate phosphatidylinositol-4-monophosphate, the 5-position thereof is then phosphorylated by the action of phosphatidylinositol-4-monophosphate-5-kinase to generate phosphatidylinositol-4,5-bisphosphate (PI-4,5-P2), which is degraded into inositol triphosphate (IP3) and diacylglycerol (DG) by extracellular stimulation. However, Cantley et al. (Rameh, L. E. and Cantley, L. C., J. Biol. Chem. Vol. 274, 8347–8350, 1999) discovered phosphatidylinositol-3-kinase (PI3K) that mediates phosphorylation at the 3-position of the inositol ring. They also demonstrated the products of this enzyme reaction, phosphatidylinositol-3-monophosphate (PI-3-P), phosphatidylinositol-3,4-bisphosphate, and phosphatidylinositol-3,4,5-triphosphate (PI-3,4,5-P3). Phosphatidylinositol-3,4-bisphosphate is also generated by dephosphorylation of the 5-position of PI-3,4,5-P3. Herein, phosphatidylinositol-3,4-bisphosphate is abbreviated as PI-3,4-P2 in principle. The structure of PI-3,4-P2 is schematically shown below.

PI-3, 4-P2

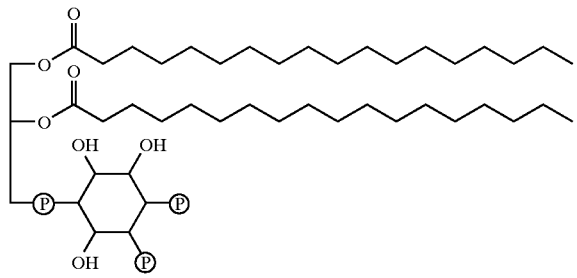

PI3K is known to be involved in the signal transduction system of insulin. It is becoming clear that PI-3,4,5-P3 and PI-3,4-P2, which are produced by the action of PI3K, an enzyme activated by a stimulus such as insulin, also activate kinases such as phosphoinositidin kinase-1 (PKD-1) and Akt/PKB to generate a survival signal that suppresses the cell death (apoptosis) (Coffer, P. J. et al., Biochem. J., Vol. 335, 1–13, 1998). This means that PI-3,4-P2 suppresses apoptosis by activating Akt/PKB and thus takes part in survival of cells.

Based on this knowledge, specific detection of these phospholipids in the cells and clarification of the dynamics thereof have been demanded to shed light on not only mechanisms of intracellular signal transduction and apoptosis but also pathogenesis of cancers and other diseases. However, no method of detecting and measuring PI-3,4-P2 exclusive of other phosphatidylinositol-polyphosphates is known.

Antibodies that specifically recognize PI-3,4-P2 are useful for purification and immunoassay of PI-3,4-P2, and serve as inhibitors of PI-3,4-P2. However, in general, poor antigenicity of phospholipids make it difficult to obtain antibodies against them. Furthermore, PI-3, 4-P2 is difficult to be obtained in large quantities. These problems have prevented the development of an immunoassay technique for PI-3,4-P2. Immunoassays are so excellent analytical methods as to achieve a high sensitivity and accuracy by a simple manipulation. For further investigation of signal transduction, an immunological assay method for PI-3,4-P2 has been strongly desired.

SUMMARY OF THE INVENTION

An objective of the present invention is to provide an antibody specifically recognizing PI-3,4-P2 and an immunological assay method using the antibody. More specifically, the present invention seeks to provide a novel antibody specifically recognizing PI-3,4-P2 and a simple method for determining PI-3,4-P2 with high sensitivity, like enzyme immunoassay, without requiring any special facilities.

Producing an anti-PI-3,4-P2 antibody is a problem because it is difficult to obtain a large quantity of antigens and the poor antigenicity of phospholipids used as antigens makes it difficult to produce an antibody of high titer. The inventors have solved the former problem by chemical synthesis of PI-3,4-P2 that enables it to be produced in large quantities. The inventors have also overcome the problem of poor antigenicity by enhancing the antigenicity using an immunogen obtained through adsorption of PI-3,4-P2 to dead Salmonella cells. In this way, the inventors have succeeded in producing a novel monoclonal antibody that binds specifically to PI-3,4-P2. Using the antibody, an immunological assay specific to PI-3,4-P2 in the living organism can be performed successfully. Furthermore, the inventors have isolated a gene encoding the amino acid sequence that constitutes variable regions of the antibody and have determined the nucleotide sequence, which will enable producing recombinant antibodies. The inventors have also found that topological PI-3,4-P2 distribution in cells can be identified and inhibitors specific to the function of PI-3,4-P2 can be developed, using the antibody of the present invention.

Specifically, the present invention relates to the following antibody, monoclonal antibody, variable regions thereof, hybridoma producing the antibody, and an immunological assay method using the antibody.

(1) An antibody specifically recognizing phosphatidylinositol-3,4-biphosphate.

(2) The antibody of (1), wherein the antibody is a monoclonal antibody.

(3) The antibody of (2), which recognizes an antigenic determinant comprising an inositol group and a glycerol backbone in phosphatidylinositol-3,4-biphosphate.

(4) The antibody of (1), which is substantially non-cross-reactive with at least one compound selected from the group consisting of phosphatidylinositol-4,5-bisphospate, phosphatidylinositol-3,4,5-triphosphate, phosphatidylinositol-1,4,5-triphosphate, and phisphatidylinositol-1,3,4,5-tetraphosphate.

(5) A hybridoma producing the antibody of (2).

(6) The hybridoma of (5), which has the properties of the deposit identified by the accession No. FERM-BP-6849.

(7) A method of producing the antibody of (2), the method comprising culturing the hybridoma of (5).

(8) A variable region of immunoglobulin heavy chain specifically binding to phosphatidylinositol-3,4-biphosphate, comprising an amino acid sequence set forth in SEQ ID NO: 2 or an amino acid sequence of SEQ ID NO: 2 in which one or more amino acid residues are substituted, deleted or added.

(9) A variable region of immunoglobulin light chain specifically binding to phosphatidylinositol-3,4-biphosphate, comprising an amino acid sequence set forth in SEQ ID NO: 4 or an amino acid sequence of SEQ ID NO: 4 in which one or more amino acid residues are substituted, deleted or added.

(10) CDR1 in immunoglobulin heavy chains specifically binding to phosphatidylinositol-3,4-biphosphate, comprising an amino acid sequence set forth in SEQ ID NO: 5 or an amino acid sequence of SEQ ID NO: 5 in which one or more amino acid residues are substituted, deleted or added.

(11) CDR2 in immunoglobulin heavy chains specifically binding to phosphatidylinositol-3,4-biphosphate, comprising an amino acid sequence set forth in SEQ ID NO: 6 or an amino acid sequence of SEQ ID NO: 6 in which one or more amino acid residues are substituted, deleted or added.

(12) CDR3 in immunoglobulin heavy chains specifically binding to phosphatidylinositol-3,4-biphosphate, comprising an amino acid sequence set forth in SEQ ID NO: 7 or an amino acid sequence of SEQ ID NO: 7 in which one or more amino acid residues are substituted, deleted or added.

(13) CDR1 in immunoglobulin light chains specifically binding to phosphatidylinositol-3,4-biphosphate, comprising an amino acid sequence set forth in SEQ ID NO: 8 or an amino acid sequence of SEQ ID NO: 8 in which one or more amino acid residues are substituted, deleted or added.

(14) CDR2 in immunoglobulin light chains specifically binding to phosphatidylinositol-3,4-biphosphate, comprising an amino acid sequence set forth in SEQ ID NO: 9 or an amino acid sequence of SEQ ID NO: 9 in which one or more amino acid residues are substituted, deleted or added.

(15) CDR3 in immunoglobulin light chains specifically binding to phosphatidylinositol-3,4-biphosphate, comprising an amino acid sequence set forth in SEQ ID NO: 10 or an amino acid sequence of SEQ ID NO: 10 in which one or more amino acid residues are substituted, deleted or added.

(16) An immunogen composition for use in producing an antibody specifically recognizing phosphatidylinositol-3,4-biphosphate, comprising a mixture of a dead Salmonella cell as an adjuvant and phosphatidylinositol-3,4-biphosphate.

(17) A method for producing an antibody specifically recognizing phosphatidylinositol-3,4-biphosphate, the method comprising using an immunogen composition of (16) for immunization.

(18) An immunoassay method which comprises the steps of reacting the antibody specifically recognizing phosphatidylinositol-3,4-biphosphate or a variable region thereof with phosphatidylinositol-3,4-biphosphate present in a sample, and detecting the binding based on an immunological reaction between the antibody or a variable region thereof and the biphosphate.

(19) An immunoassay method of (18), which comprises observing the degree to which the immunological reaction between the antibody or a variable region thereof and an antigenic determinant recognized thereby is inhibited by phosphatidylinositol-3,4-biphosphate present in a sample.

(20) A kit for immunoassay for phosphatidylinositol-3,4-biphosphate comprising the antibody specifically recognizing phosphatidylinositol-3,4-biphosphate or a variable region thereof.

BRIEF DESCRIPTION OF THE DRAWINGS

FIG. 6 schematically shows a putative hyper variable region (complementarity determining region (CDR)) in the variable region in each of the light chains and the heavy chains of the monoclonal antibody 8C2.

FIGS. 7A–7L are photographs showing the results of immunostaining of PI-3,4-P2 induced by the $H_2O_2$ treatment; FIGS. 7A–7F represent the case with no addition of wartmannine, and FIGS. 7G–7L represent the case with addition of wartmannine.

FIGS. 8A–8H are photographs showing the specificities of 8C2 determined by the competitive reaction with PI-3,4,-P2 analogs. FIGS. 8A and 8B represent the case with no competitive compound, FIGS. 8C and 8D the case with 50 μM phosphatidylcholine, FIGS. 8E and 8F the case with 50 μM PI-3,4,-P2, and FIGS. 8G and 8H the case with 50 μM PI-4,5,-P2.

DETAILED DESCRIPTION OF THE INVENTION

Figure 1:
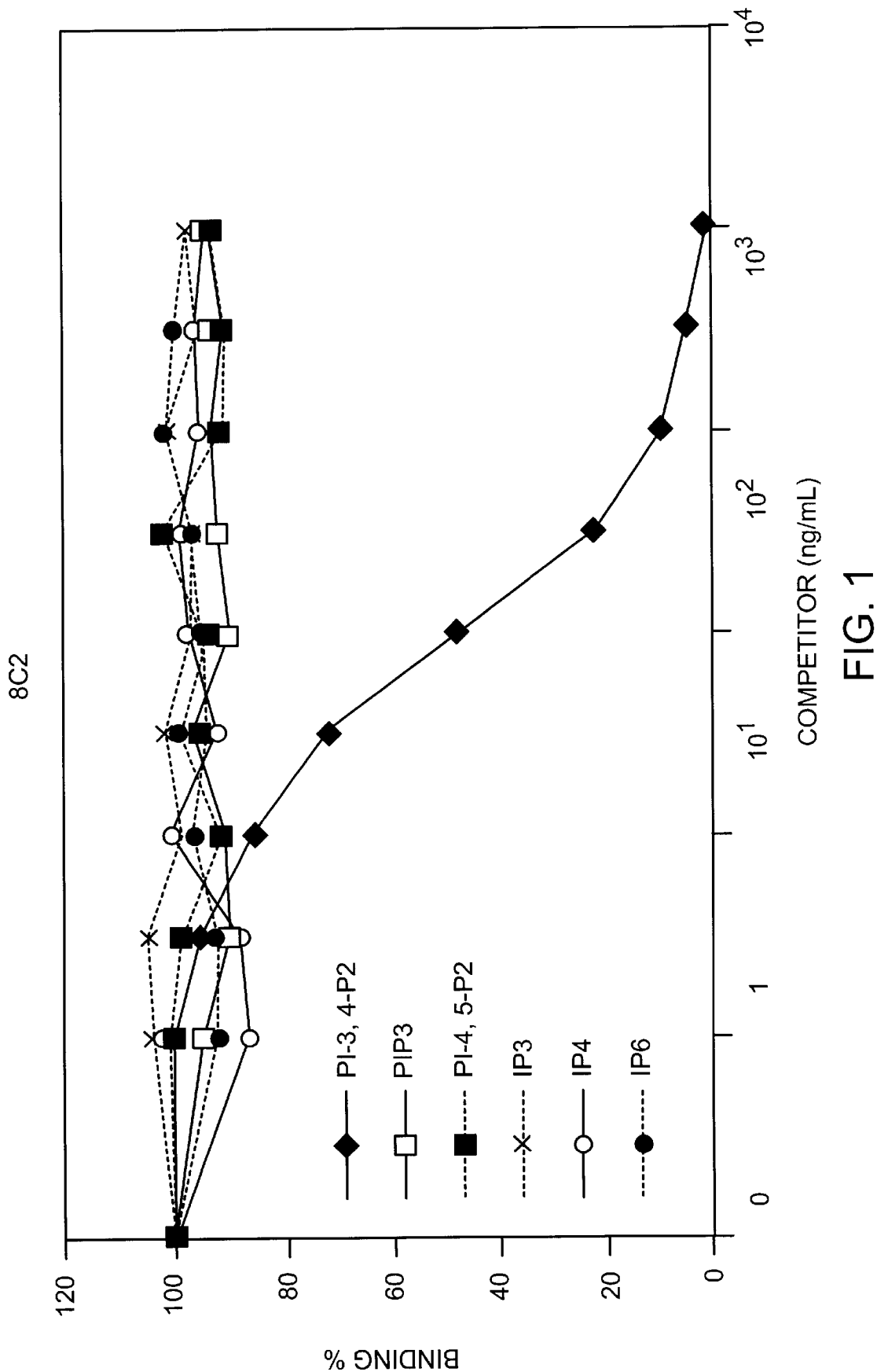
FIG. 1 is a graph showing the results of indirect enzyme-linked immunosorbent assay (hereinafter referred to as ELISA) performed to verify the cross-reactivity of the antibody 8C2 with various inositol polyphosphates. The ordinate designates the binding (%) of the antibody 8C2, and the abscissa designates the concentration (ng/mL) of competitive compounds.

The antibody of the present invention specifically recognizes PI-3,4-P2 but is not substantially cross-reactive with PI-4,5-P2. Throughout the specification, the term "specific to PI-3,4-P2" means that the antibody can recognize the phosphorylated state of PI-3,4-P2 and immunologically distinguish PI-3,4-P2 from other phosphorylated compounds. The antibody of the present invention can be produced by the following immunological procedures. PI-3,4-P2 is suspended together with the killed Salmonella cells, and the resulting suspension is used as an immunogen. In more detail, lipopolysaccharides are removed from the dead Salmonella cells (Galanos C., Eur. J. Biochem., 24, 116–122, 1971). PI-3,4-P2 is then coated onto the dead cells to prepare a suspension for use as an immunogen (Umeda M., J. Immun., 137, 3264–3269, 1986). PI-3,4-P2 may be purified from cells or chemically synthesized. PI-3,4-P2 can be produced in accordance with the methods for synthesizing known compounds with similar structures to PI-3,4-P2 (Thum O., Chen J., Prestwich G. D., Tetrahedron Lett. 37, 9017–9020, 1996; Shirai R. et al. ibid. 39,9485–9488,1998, Shirai R. et al., ibid. 40, 1693–1696, 1999; Sawada T. et al., Chem. Pharm. Bull. 45, 1521–1523, 1997). An animal suitable for immunization is immunized with PI-3,4-P2. When the antibody titer increased, the blood sample is collected. The antibody may be polyclonal or monoclonal. The monoclonal antibody is more advantageous in that an antibody with a higher specificity can be selected. Furthermore, when the monoclonal antibody is established, it enables cloning cDNA coding for the amino acid sequences that constructs the variable regions of the monoclonal antibody having a desired binding activity, as will be described later.

The monoclonal antibody can be produced by cloning antibody-producing cells. In general, antibody-producing cells taken out from the immunized animal are subjected to cell fusion with an appropriate fusion partner. The resulting hybridomas are then screened in terms of the activity of the produced antibodies (Gulfre G., Nature, 266, 550–552, 1977). When mice are employed as the animal for immunization, mouse-derived myeloma cells such as P3-X63-Ag.653 are adequate as the fusion partner. The hybridomas subjected to HAT selection are screened first in terms of the binding activity to PI-3,4-P2. The hybridomas producing the antibodies that have the binding activity to PI-3,4-P2 are then subjected to a cross-reactivity test. In this test, the binding activity to other phospholipid antigens is examined to screen hybridomas having an acceptable cross-reactivity. Acceptable cross-reactivity means a cross-reactivity that can be disregarded for the desired use of the antibody. When the monoclonal antibody is employed for an immunological assay, it has no substantial cross-reactivity if a signal provided by the cross-reactivity is reduced to the level of the background in the final assay system.

A desired antibody of the present invention is not substantially cross-reactive with the compounds shown below, which are structurally similar to PI-3,4-P2. A particularly preferable antibody of the present invention, as described in Examples below, distinguishes PI-3,4-P2 from any of these similar compounds:

phosphatidylinositol-4,5-bisphosphate;
phosphatidylinositol-3,4,5-triphosphate;
phosphatidylinositol-1,4,5-triphosphate; and
phosphatidylinositol-1,3,4,5-tetraphosphate.

ELISA or liposome lysis assay is useful for verifying the reactivity of the antibody to PI-3,4-P2 or the cross-reactivity with other phospholipid antigens. In ELISA, microtiter plates coated with an antigen whose reactivity is to be observed are prepared. A sample solution obtained by suitably diluting the hybridoma supernatants is then added to the wells of the microtiter plates to initiate a reaction. After a thorough reaction, the wells are washed, and a second antibody to immunoglobulin is then added for further reaction. The second antibody finally bound to each well is assayed. Thus, the binding activity of the antibody present in the culture supernatant to the antigen can be quantitatively determined. ELISA has been demonstrated for an antibody using a phospholipid antigen (Umeda M., J. Immun., 136, 2562–2567, 1986).

The liposome lysis assay utilizes the phenomenon that when an antibody reacts with an antigen-coated liposome, the liposome lyses by the action of the complement. Since the action of the complement is utilized, the technique is called complement-dependent liposome lysis assay. Liposomes comprise phospholipid antigens to be examined in addition to dicetyl phosphate (hereinafter abbreviated as DCP), dimyristoyl phosphatidylcholine (hereinafter abbreviated as DMPC), and cholesterol. These lipid components are dissolved in an appropriate organic solvent. The solution is then dried to prepare a lipid film. When the film is added to an aqueous solvent and the mixture is agitated vigorously, liposomes of multilamellar structure are formed. In the liposomes thus prepared, phospholipid antigens are taken up as membrane-constructing components. For this reason, an antigenic structure close to the antigen present in actual cell membranes is presented. It is thus appropriate for screening the monoclonal antibody. For easy screening, a fluorescent dye can be enclosed in the liposomes as a lysis marker. Typical examples of the fluorescent dye include 4-methylumbelliferyl phosphate and calcein. When the antibody binds to this liposome-constructing phospholipid antigen in the presence of its complement, the liposome is broken down to release the fluorescent dye in the liposome. This phenomenon is observed as increased fluorescence intensity in the liquid phase. Complement-dependent liposome lysis assay using phospholipid antigens such as PI-4,5-P2 is known (Molec. Immun., 26, 1025–1031, 1988). The phospholipids used to verify the cross-reactivity are phospholipid antigens having a similar structure. The cross-reactivity should be verified with analogous substances having a similar partial structure. Specific examples of such compounds are given below, and their structural characteristics will be shown in examples below.

| | |
|---|---|
| PC | phosphatidylcholine |
| PS | phosphatidylserine |
| PA | phosphatidic acid |
| PI | phosphatidylinositol |
| PE | phosphatidylethanolamine |
| PI-4,5-P2 | phosphatidylinositol-4,5-bisphosphate |
| IP3 | 1,4,5-inositol triphosphate |
| IP4 | 1,3,4,5-inositol tetraphosphate |
| IP6 | 1,2,3,4,5,6-inositol hexaphosphate |

In both ELISA and liposome lysis assay, the cross-reactivity of the antibody with other phospholipid antigens can be verified by the reaction system using PI-3,4-P2 as an antigen. That is, to the reaction system containing PI-3,4-P2 and the antibody to be examined for its specificity are added other antigens to be examined for the cross-reactivity with the antibody and the competitive reaction is then observed to confirm the cross-reactivity. This technique for verifying the cross-reactivity by means of the competitive inhibition is useful for rapid screening since it is unnecessary to prepare the reaction system for all antigens.

The procedures described above can yield an antibody of the present invention that has binding activity to PI-3,4-P2 and can immunologically distinguish PI-3,4-P2 from structurally similar antigens such as PI-4,5-P2.

The monoclonal antibody of the present invention is produced by, for example, the hybridoma 8C2-FNL, which has been deposited under accession No. FERM BP-6849. The monoclonal antibody of the present invention can be obtained from a hybridoma by culturing the hybridoma cells under appropriate conditions and collecting the antibodies produced by the cells. If the hybridoma is a homohybridoma, it can be inoculated into syngeneic animals intraperitoneally and cultured in vivo. In this case, monoclonal antibodies are collected as ascitic fluid. In the case of heterohybridomas, such cells can be cultured in vivo using a nude mouse as a host.

In vitro culture, as well as in vivo culture, is commonly performed in an appropriate culture environment. An essential medium such as RPMI1640 or DMEM is typically used as a culture medium for hybridomas. Additives such as animal sera may be added to the medium to maintain high antibody productivity. Monoclonal antibodies can be recovered from culture supernatant of In vitro culture of hybridoma. Culture supernatant can be harvested by either separating it from cells after culturing or successively collecting it during culturing when a hollow fiber culture system is used.

Monoclonal antibodies collected as ascitic fluid or culture supernatant are fractionated by salting out with saturated ammonium sulfate to isolate the immunoglobulin fraction, and then subjected to purification processes such as gel filtration and ion-exchange chromatography to obtain the monoclonal antibody of the present invention. If the monoclonal antibodies are IgGs, other purification methods such as affinity chromatography using protein A or G column are also effective.

The present invention further provides the amino acid sequences constituting the variable regions of the novel antibody having a desired binding activity to PI-3,4-P2 and the nucleotide sequences encoding the same. More specifically, the present invention provides the immunoglobulin variable regions containing the amino acid sequences set forth in SEQ ID NO: 2 and SEQ ID NO: 4. The present invention further provides cDNA encoding the immunoglobulin variable regions containing the nucleotide sequences set forth in SEQ ID NO: 1 and SEQ ID NO: 3. SEQ ID NO: 1 and SEQ ID NO: 2 are deduced from the heavy chain and, SEQ ID NO: 3 and SEQ ID NO: 4 from the light chain, in the immunoglobulin molecule. These amino acid sequences or cDNA nucleotide sequences are not necessarily identical but may vary so long as the specific binding activity to PI-3,4-P2 is maintained. As will be later described, particularly the site corresponding to CDR is highly variable. In the CDR region, even amino acids may vary some occasions.

In general, each immunoglobulin molecule consists of heavy chains having a larger molecular weight and light chains having a smaller molecular weight. The heavy and light chains each carries a region called "a variable region" in about 110 amino acid residues at the N-terminus, which are different between the molecules. Variable regions of a heavy chain and a light chain are designated VH and VL, respectively. The antigen-binding site is formed by forming a dimer through electrostatic interaction between the heavy chain variable region VH and the light chain variable region VL. The variable region consists of three complementarity determining regions (CDRs) and four frameworks. The CDR forms a complementary steric structure with the antigen molecule and determines the specificity of the antibody. The three CDRs inserted between the four framework regions (FRs) are present like a mosaic in the variable region (E. A. Kobat et al., Sequences of proteins of immunological interest, vol. I, 5th edition, NIH Publication, 1991). The amino acid sequences of FRs are well conserved, but those of CDR are highly variable and may thus be called hypervariable regions. Among the amino acid sequences of the antibody specifically recognizing PI-3,4-P2, a CDR that determines the binding activity to antigens has been clarified in the present invention. Thus, the present invention further provides the CDR shown below (numbering the N-terminal amino acid residue as 1 in SEQ ID NO: 1 or 3), in which the number in parentheses corresponds to the SEQ ID number.

| CDR  | Heavy chain | Light chain |
| ---- | ----------- | ----------- |
| CDR1 | 26–32(5)    | 24–39(8)    |
| CDR2 | 52–57(6)    | 55–61(9)    |
| CDR3 | 99–109(7)   | 94–102(10)  |

The cDNAs bearing the nucleotide sequences coding the variable regions in immunoglobulin molecules can be cloned from hybridomas that produce the monoclonal antibody to PI-3,4-P2. For example, the hybridoma of the present invention, deposited under the accession No. FERM BP-6849, is preferable as a starting material the cloning. More specifically, PCR is performed using the signal sequence of the gene in the variable regions and the nucleotide sequence in the constant regions. The amplified product is introduced into an appropriate cloning vector for further amplification to produce a library of variable genes. Since the site corresponding to CDR will be a sequence specific to the variable regions of the present invention, positive clones are screened from the library of the variable regions using the site as a probe. The resulting cDNA is inserted into a phage by linking the light and heavy chain variable region genes through an appropriate linker. Thus, the cDNA may be expressed as a single-stranded antibody (so-called scFV). Alternatively, immunoglobulins cDNA are inserted into a known vector for expression to utilize the same for producing immunoglobulins. Examples of the vector for expressing immunoglobulins without limit include a SV40 virus-based vector and a BPV (papilloma virus)-based vector. For example, BCMGS Neo vector, one of the BPV vectors (Hajime Karasuyama, "Bovine Papilloma Virus Vector" from the extra issue of JIKKEN IGAKU (Experimental Medicine): IDENSHI KOGAKU (Genetic Engineering) Handbook, edited by Masami Muramatsu & Hiroto Okayama, Yodosha Publishing Co., pp. 297–299, 1991), is desirable since the vector transfect to COS7 cells to express a foreign gene efficiently.

Alternatively, the specificity of the antibody of the present invention may also be artificially reconstructed by incorporating the CDR into the framework of an optional immunoglobulin molecule. Such a technique is called the CDR grafting antibody technique (P. T Jones et al., Nature, 321, 522, 1986) and has already been established for humanizing mouse immunoglobulins. The CDRs of the present invention include not only those completely identical but also variants so long as the specificity to PI-3,4-P2 is maintained. That is, the CDR amino acid sequences in which one or more amino acid residues are modified may also be used as the CDR sequence. The modified amino acid residues in the amino acid sequences of the CDR variant are preferably 30% or less, more preferably 20% or less, most preferably 10% or less, within the entire CDR. Any FR can be used as the FR into which the CDRs are to be incorporated. The CDRs of the present invention are originally derived from mouse immunoglobulins. However, the CDRs may be inserted into FRs of not only mouse immunoglobulins but also immunoglobulins of other species. The cDNAs encoding the variable regions thus constructed may be expressed by incorporating the same into the vectors described above.

In introducing mutations into CDRs, the above-described phage vector may be employed. The phage vector can express the antibody activity rapidly and hence can rapidly screen mutants. Moreover, the phage vector expresses the antibody molecule on the surface of host bacteria in an amount sufficient for screening. A mutation introduced into the CDRs remarkably increases the antibody binding activity. Thus, a single-stranded antibody having an improved binding activity can be produced using the CDRs of the present invention.

The variable regions and CDR-incorporated variable regions provided by the present invention may be expressed in their original forms. Alternatively, these variable regions may be expressed as complete immunoglobulin molecules by linking to a gene encoding the constant regions.

To express variable regions by the cDNA-incorporated vector or by the vector bearing the insert obtained by linking CDR alone to a certain FR, a dimer of the heavy and light chains can be produced by expressing heavy chain variable regions and light chain variable regions in the same host cell. This can be done by co-transformation of a host cell with a light chain expression vector and a humanized heavy chain expression vector. The antibody of the present invention can be produced from the transformant. Preferred examples of the host for the transformation include Chinese hamster ovary (CHO) cells (A. Wright & S. L. Morrison, J. Immunol., 160, 3393–3402, 1998) and SP2/0 cells (mouse myeloma) (K. Motmans et al., Eur. J. Cancer Prev., 5, 512–519, 1996; R. P. Junghans et al., Cancer Res., 50, 1495–1502, 1990). The transformation can be performed by the lipofectin method (R. W. Malone et al., Proc. Natl. Acad. Sci. USA, 86,6077, 1989, P. L. Felgner et al., Proc. Natl. Acad. Sci. USA, 84, 7413, 1987), the electroporation method, the calcium phosphate method (F. L. Graham & A. J. van der Eb, Virology, 52, 456–467, 1973), or the DEAE-Dextran method.

When the expressed variable region is accompanied by the constant region, the expression product may be purified through a protein A column, a protein G column, an anti-immunoglobulin antibody affinity column, etc. to recover the product as a purified protein. When only the variable region is expressed, these techniques for purification do not apply. In that case, other suitable purification methods should be selected. For example, if the variable region is expressed as the product fused to a protein such as a histidine tag at the C-terminus, then the expression product is purified by affinity chromatography using the corresponding ligand.

According to the present invention, PI-3,4-P2 can be immunologically assayed using the thus produced monoclonal antibody or variable regions thereof. Immunological assay of PI-3,4-P2 was impossible by conventional methods since an antibody itself specific to PI-3,4-P2 was not available. The antibody of the present invention provides excellent specificity to PI-3,4-P2 and hence provides an ideal immunological method for assaying PI-3,4-P2.

According to the present invention, PI-3,4-P2 can also be assayed by observing the degree of PI-3,4-P2 inhibition, utilizing the phenomenon that the binding between PI-3,4-P2 and the antibody of the present invention (including the variable regions) is inhibited by PI-3,4-P2 originating from a sample to be analyzed. One inhibition assay that realizes such an assay principle utilizes immobilized PI-3,4-P2. In more detail, PI-3,4-P2 is adsorbed onto a container like a microtiter plate. A sample solution is added to the plate. PI-3,4-P2 can be physically adsorbed onto the container wall after it is dissolved in an appropriate carrier such as phosphatidylcholine. The antibody of the present invention is then added, causing a competitive reaction between PI-3,4-P2 adsorbed on the container and PI-3,4-P2 in the sample solution with the antibody of the present invention. The antibody bound (or unbound) to the solid phase can be readily assayed by labeling the antibody with an appropriate marker. The quantity of PI-3,4-P2 present in the sample solution can then be determined by comparison with the results obtained from a standard solution. The antibody can be labeled with a marker such as an enzyme, a fluorescence or a luminiferous substance. PI-3,4-P2 can be assayed in a biological sample solution such as a tissue, a cultured cell, or a body fluid like blood or serum. The foregoing competitive reaction may also be performed by immobilizing the antibody of the present invention onto the wall of a container. In this case, the labeled PI-3,4-P2 is reacted with the antibody concurrently with a PI-3,4-P2-containing sample.

The sample for the immunological assay may be either liquid or solid. For example, a tissue specimen is immunologically stained to observe the presence or absence of PI-3,4-P2 or localization of PI-3,4-P2. In a preferred embodiment, the antibody of the present invention recognizes the epitope formed by the inositol group and the glycerol backbone of PI-3,4-P2. Since the epitope is assumed to be exposed on the surface of the cell membrane, the antibody is useful for staining a tissue specimen. In this case, localization of several phospholipids may be observed in the same sample by using the antibody in combination with another antibody specifically recognizing a phospholipid, e.g., PI-4,5-P2. A known double-staining technique involves staining the same sample using different antibodies each labeled with fluorescent dyes having different wavelengths.

The present invention further provides a kit for use in the immunoassay described above. More specifically, the kit of the present invention comprises the antibody of the present invention, a substrate required for detecting the label, positive control, negative control, and a buffered solution used for diluting and washing a sample.

The present invention provides a monoclonal antibody that specifically binds to PI-3,4-P2. The present invention further provides an immunological assay method using the antibody. The experimental results revealed that the antibody recognizes, as the epitope, not only the inositol group but also the glycerol backbone of PI-3,4-P2. Thus, the antibody of the present invention can distinguish PI-3,4-P2 from other inositol compounds.

The present invention further provides the gene encoding the variable regions of the antibody and hence enables producing recombinant antibodies. Since the antibody of the present invention is highly specific to PI-3,4-P2, the location of PI-3,4-P2 in cells can be identified. Alternatively, signal transduction by PI-3,4-P2 to the downstream can be inhibited using the specificity of the antibody to PI-3,4-P2 to investigate any affect caused. The present invention facilitates conducting studies that could not be conducted by conventional assay methods.

The present invention will be described below in more detail with reference to examples. However, this invention is not to be construed to be limited to those examples.

EXAMPLE 1

Producing Anti-PI-3,4-P2 Monoclonal Antibody

To produce anti-PI-3,4-P2 antibody, synthesized PI-3,4-P2 was coated onto dead Salmonella cells as an adjuvant. The coated cells were then used as an immunogen. Namely, Salmonella minnesota was cultured overnight and collect the cells. The cells were centrifuged and washed twice with distilled water and once with diethyl ether, then dried in vacuo. The cells were then dispersed in a 1% aqueous acetic acid solution. The dispersion was heated at 100° C. for 2 hours to remove liposaccharide-linked oligosaccharides (Galanos C., Eur. J. Biochem., 24, 116–122, 1971). The thus treated cells were washed and coated with 4 µg of PI-3,4-P2 per 50 µg cells. The resulting suspension was used as the immunogen (for single-use) (Umeda M., J. Immun., 137, 3264–3269, 1986). PI-3,4-P2 was chemically synthesized by the known method (Thum O., Chen J., Prestwich G. D., Tetrahedron Lett. 37, 9017–9020, 1996; Shirai R. et al. ibid. 39, 9485–9488, 1998, Shirai R. et al., ibid. 40, 1693–1696, 1999; Sawada T. et al., Chem. Pharm. Bull. 45, 1521–1523, 1997). The immunogen was injected into Balb/c mice via the tail veins a few times every other week. In the mice with an increased antibody titer, the spleen cells were fused with myeloma cells P3-X63-Ag.653 to produce hybridomas.

Following the HAT selection, hybridoma supernatants were screened for the antibodies in terms of the binding activity to PI-3,4-P2. The binding activity of the antibodies was screened by liposome lysis assay. At the same time, the antibodies that produced positive clones were tested for the cross-reactivity by indirect ELISA.

In the liposome lysis assay, PI-3,4-P2 (<1%), phosphatidylcholine (40%), cholesterol (40%) and dicetyl phosphate (10%) were dissolved in chloroform and distilled to dryness under reduced pressure to prepare a lipid film. After a highly concentrated aqueous solution of calcein (fluorescent dye) was added to the film, the mixture was vigorously stirred to prepare calcein marker-enclosed multilamellar liposomes. The culture supernatant was added to the liposomes together with the complement so that the antigen-antibody binding occurred to activate the complement and break the membrane. When the antibody bound to PI-3,4-P2 is present in the culture supernatant, the highly concentrated calcein in the liposomes is released so that the concentration of calcein is reduced, causing fluorescence to be emitted. By measuring the fluorescent intensity, the activity of the antibody with respect to the antigen was determined.

Indirect ELISA was performed as follows. First, a solution of 100 ng/mL of PI-3,4-P2 in 5 µg/mL of phosphatidylcholine (carrier) was added in microtiter plates. It was allowed to stand overnight at room temperature for coating, then dried. The wells were then incubated with blocking buffer (1% bovine serum albumin (BSA), 10 mM Hepes-buffered saline (HBS, pH 7.6)) for 30 minutes at room temperature. The blocked antigen-coated plates were washed, sealed and stored in a refrigerator until use.

After 100 µL each of PIP, PI-4,5-P2, IP3, IP4 and IP6 (serially diluted to $10^0$ to $10^4$ ng/mL with 0.5% BSA/HBS) and 100 µL of hybridoma supernatants were added to the wells of the antigen-sensitized plates, incubation was carried out at room temperature for 2 hours. The reaction solution was removed. After washing with HBS, a second antibody (alkaline phosphatase-labeled anti-mouse IgG3 or anti-mouse IgM; diluted to 1/2000 with 0.5% BSA/HBS) was added to the system followed by incubation at room temperature for 2 hours. After completion of the reaction, the unreacted antibodies were removed. The wells were again washed with HBS, and p-nitrophenyl phosphate (PNPP) was added to the wells to measure the activity of the alkaline phosphatase remaining in the wells. When the antibody contained in the culture supernatants was specific to PI-3,4-P2, the immune reaction between the antibody and PI-3,4-P2 proceeded without competitive inhibition by the various co-existing compounds. Thus, the higher alkaline phosphatase activity is retained in the solid phase. In contrast, when the antibody was not reactive with PI-3,4-P2 or was cross-reactive with the various co-existing antigens, the number of antibodies that reacted with PI-3,4-P2 on the solid phase was reduced due to competitive inhibition. As a result, the alkaline phosphatase activity retained on the solid phase became lower. The results of the culture supernatant of hybridoma 8C2-FNL obtained by ELISA are shown in FIG. 1. Since 8C2-FNL produces the antibody that reacts only with PI-3,4-P2, a concentration-dependent decrease in binding percent (taking the absorbance obtained with the culture supernatant alone as 100%) is observed only for PI-3,4-P2.

By this screening, four clones that produced an antibody reactive only with PI-3,4-P2 were established. Designations of these clones are summarized in the table below. The relative reactivity of the clone to PI-3,4-P2 was defined as the inverse of the concentration (ml/µg) required for lysis of 40% of the liposomes. The reactivity of the antibody produced by the 8C2-FNL (Hereinafter, 8C2 denotes a monoclonal antibody unless otherwise noted.), which showed the highest reactivity to PI-3,4-P2, was further investigated.

| Clone | Class | Relative reactivity to PI-3, 4-P2 |
|---|---|---|
| 8C2 | IgG3 | 417 |
| 12D10 | IgG3 | 12 |
| 3E10 | IgG3 | 26 |
| 3C7 | IgG2b | 83 |

EXAMPLE 2

Specificity of Anti-PI-3.4-P2 Monoclonal Antibody 8C2 (IgG3)

Among the antibodies obtained in Example 1, 8C2 reacted only with PI-3,4-P2 and showed the highest specificity to PI-3,4-P2. The reactivity of this antibody was further analyzed by liposome lysis assay. Prior to the assay, pristane-treated mice were intraperitoneally inoculated with hybridoma 8C2-FNL. Immunoglobulin was purified from the ascetic fluid by ammonium sulfate fractionation and used as monoclonal antibody 8C2. The following lipid antigens were used for the liposome lysis assay.

phosphatidylcholine (PC)
phosphatidylserine (PS)
phosphatidic acid (PA)
phosphatidylinositol (PI)
phosphatidylethanolamine (PE)

Figure 2:
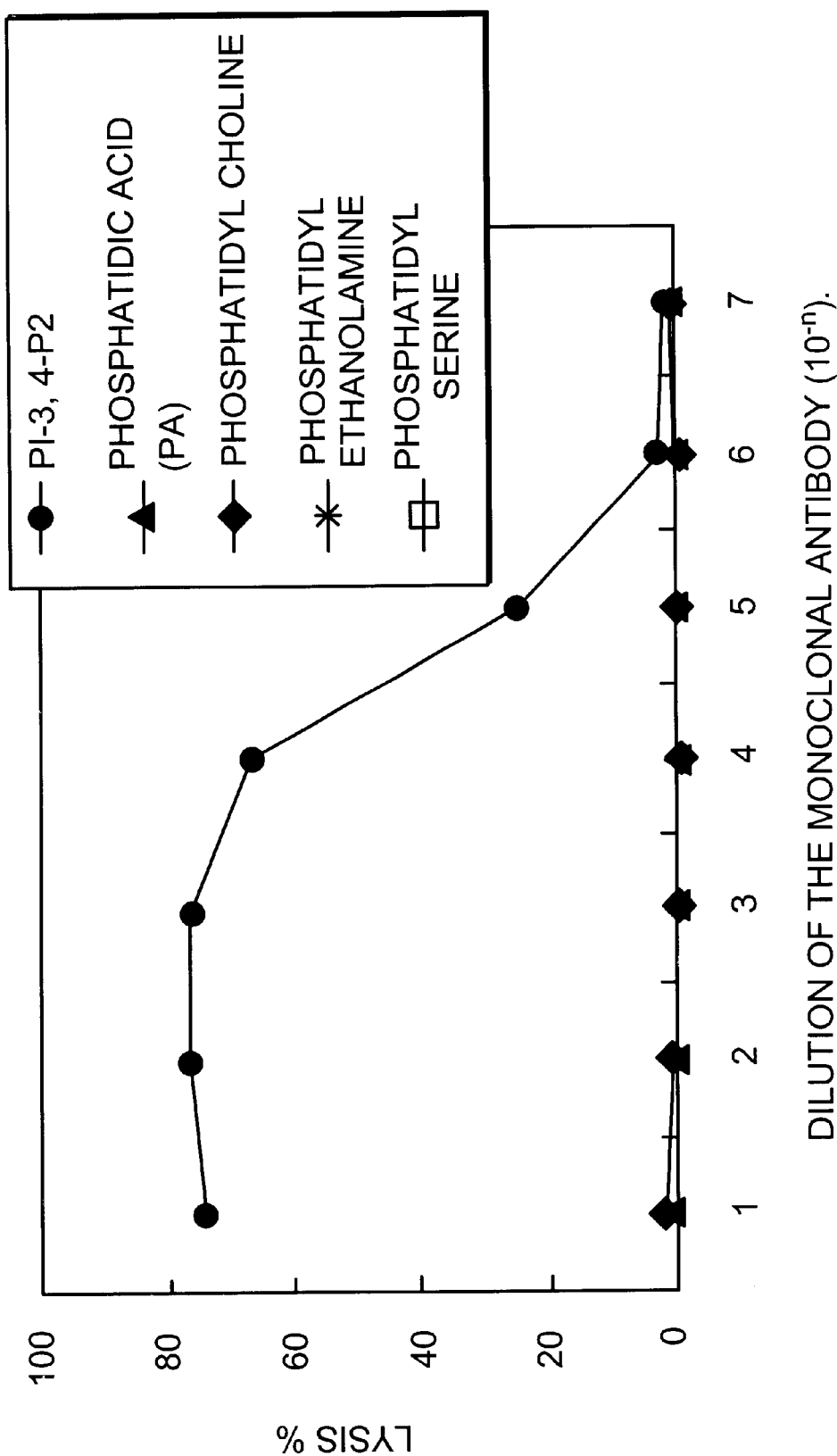
FIG. 2 is a graph showing the results of liposome lysis assay performed to verify the binding activity of the antibody 8C2 to various phospholipids with similar structures. The ordinate designates the lysis (%) of liposomes, and the abscissa designates the dilution ($10^{-n}$) of the antibody.

Liposomes prepared for the assay consisted of 50% cholesterol and 40% phosphatidylcholine as the main constituents and 10% of various different lipids as the remaining constituents. The liposomes different in composition were prepared in the same manner. The binding activity of 8C2 was assayed by varying dilution of the antibody within $10^{-1}$ to $10^{-7}$ based on the liposomes. Lysis of the liposomes was observed to be concentration-dependent only in the liposomes containing PI-3,4-P2. In contrast, no lysis was observed in the liposomes containing other membrane-constructing phospholipids such as PC, PS, PA, PI, or PE, even when using the dilution with the highest antibody concentration ($10^{-1}$) prepared for the assay. The results are shown in FIG. 2. In FIG. 2, liposome lysis (%) refers to a percentage when the fluorescent intensity is made 100% when all of the liposomes reacted were lysed. The results reveal that 8C2 reacted only with PI-3,4-P2 in the phospholipids. To obtain more detailed information on an epitope recognized by 8C2, the cross-reactivity of phosphatidylinositol with various phosphorylated antigen derivatives was examined.

Liposomes prepared for the assay consisted of 50% cholesterol, 40% phosphatidylcholine, and 9% dicetyl phosphate as the main constituents and 1% of the following phosphorylated derivatives as the remaining constituents.

PI

PI4P (phosphatidylinositol phosphate)

PI-3,4-P2

PI-4,5-P2

N-PIP3 (natural PIP3, purchased from Alexis)

S-PIP3 (chemically synthesized PIP3)

PA (phosphatidic acid)

PC

PE

PS cardiolipin

Figure 3:
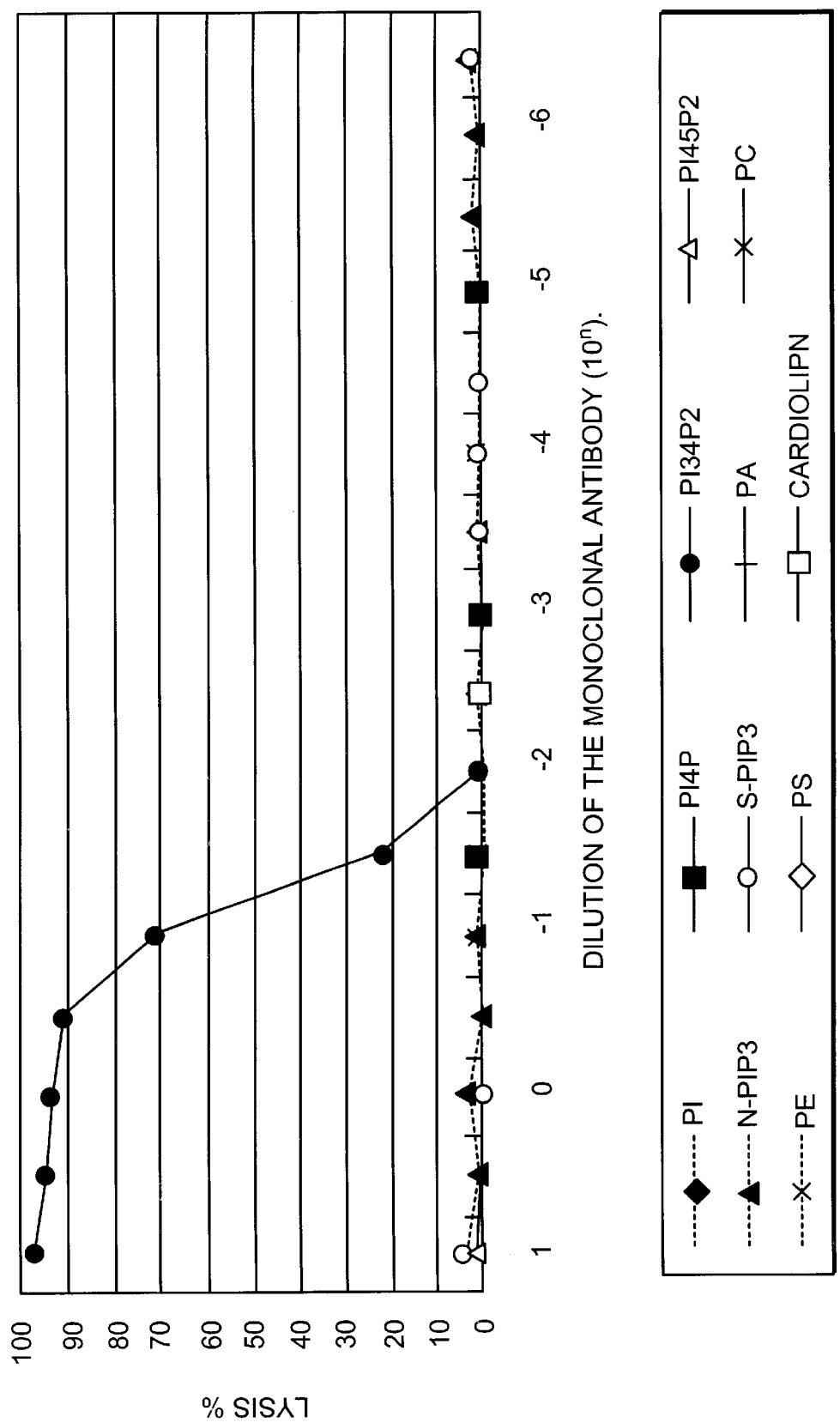
FIG. 3 is a graph showing the results of liposome lysis assay performed to verify the binding activity of the antibody 8C2 to various compounds with similar structures. The ordinate designates the lysis (%) of liposomes, and the abscissa designates the dilution ($10^{-n}$) of the antibody.

The assay was performed by varying the antibody dilution from $10^{-1}$ to $10^{-6}$. As in the previous experiment, lysis of the liposomes was observed to be concentration-dependent in the liposomes containing PI-3,4-P2. However, no reaction was observed in the liposomes containing any other phospholipids, even when the dilution with the highest antibody concentration prepared for the assay was used (FIG. 3). The antibody exhibited only 1% or less cross-reactivity to PI-4,5-P2, which is structurally very similar to PI-3,4-P2, compared with the reactivity to PI-3,4-P2. The foregoing results reveal that the phosphate group at the 4-position of the inositol group plays the important role for antigen recognition of 8C2, and that the phosphate group at the 3-position also participates in the epitope configuration.

EXAMPLE 3

Epitope of Anti-PI-3.4-P2 Monoclonal Antibody 8C2 (IgG3)

To identify the recognition site of the 8C2 antibody, the above liposome lysis assay was performed using as competitors inositol polyphosphates (30 nM, 100 nM, 300 nM, 1 μM, 3 μM, and 10 μM) having a similar configuration to the inositol group of PI-3,4-P2. The inositol polyphosphates used are given below.

inositol-1,4,5-triphosphate (IP3)

inositol-1,3,4,5-tetraphosphate (IP4)

inositol-1,2,3,4,5,6-hexaphosphate (IP6)

Figure 4:
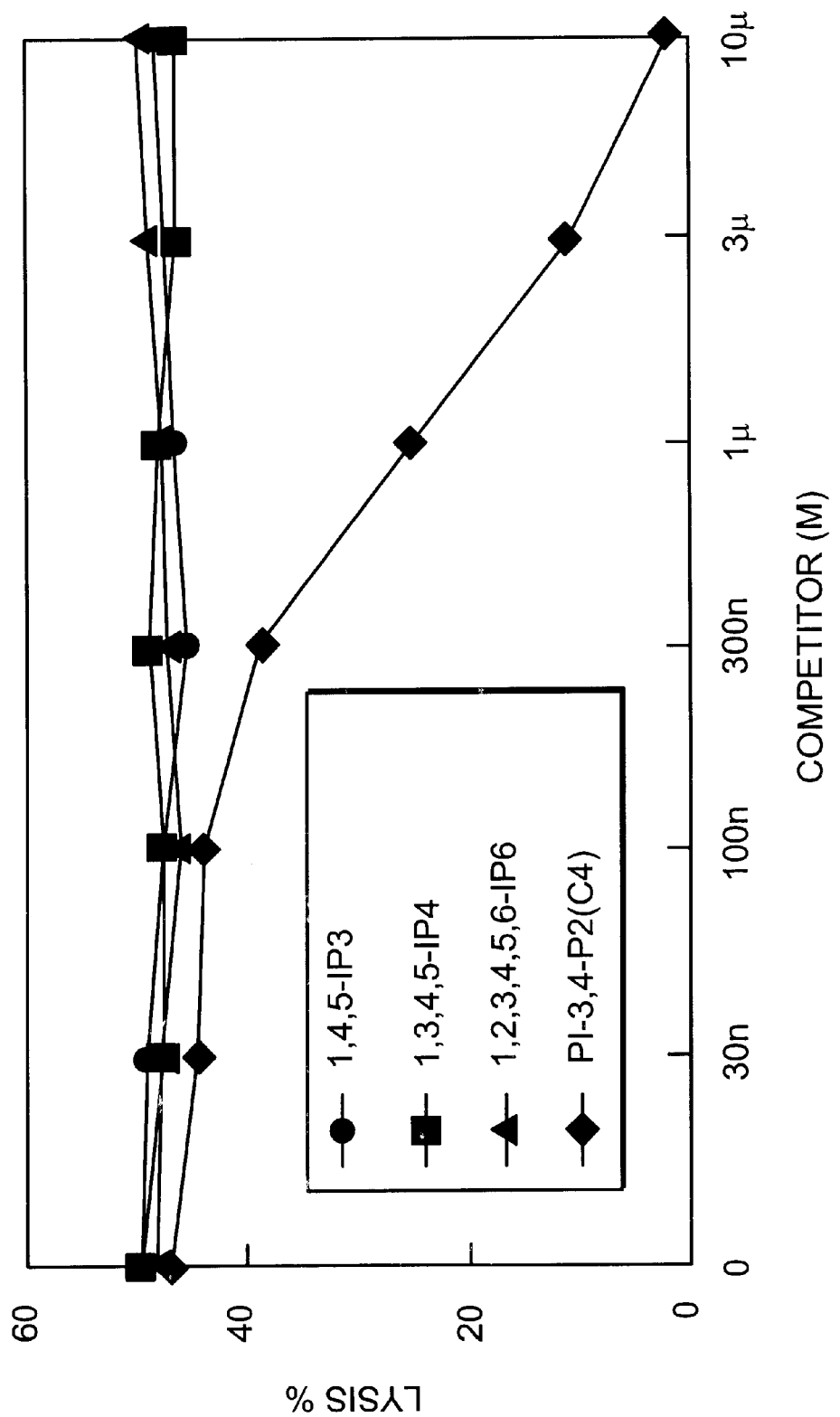
FIG. 4 is a graph showing the reactivity of the antibody 8C2 to inositol compounds with similar structures using the competitive reaction in the liposome lysis assay. The ordinate designates the lysis (%) of liposomes, and the abscissa designates the concentrations (M) of the competitive compounds.

When free PI-3,4-P2 was added as the competitor, absorbance was reduced in a concentration-dependent manner by competition with the fixed PI-3,4-P2. Other inositol polyphosphates, such as IP3, IP4 and IP6, were not affected, as shown in FIG. 4.

These results suggest that the glycerol backbone is involved in the recognition site of the antibody. Since the absorbance reduction depended on the concentration of PI-3,4-P2 added, the antibody of the present invention makes the immunoassay possible, based on the competitive reaction of PI-3,4-P2. Furthermore, the antibody of the present invention is not affected by various other compounds having similar configurations. Thus, the present invention can provide a simple assay system which is excellent in specificity to PI-3,4-P2.

To determine whether the side chains of PI-3,4-P2 constitute a recognition site for the antibody, phosphatidylserine (PS) and PI-3, 4-P2 with side chains of different length were examined for their reactivity by liposome lysis assay. The experiments were conducted using the compounds of the formulae shown below in which the lengths of the side chains are different:

PS

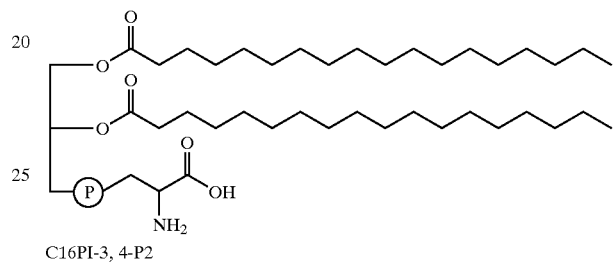

C16PI-3, 4-P2

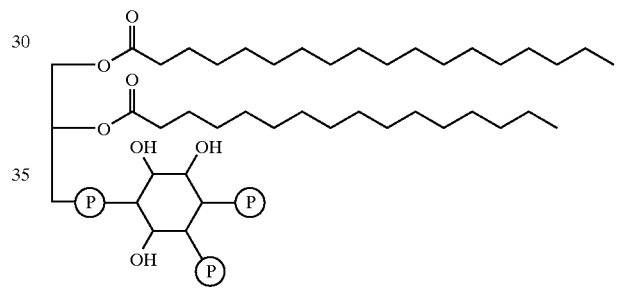

C4PI-3, 4-P2

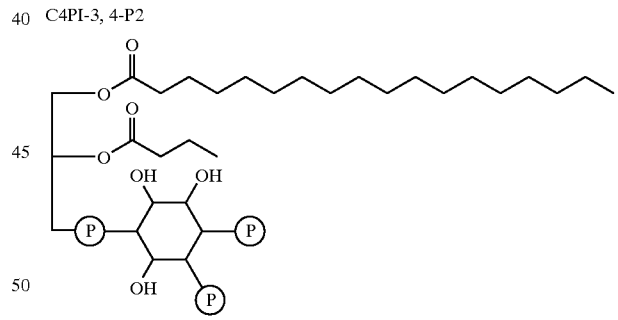

Figure 5:
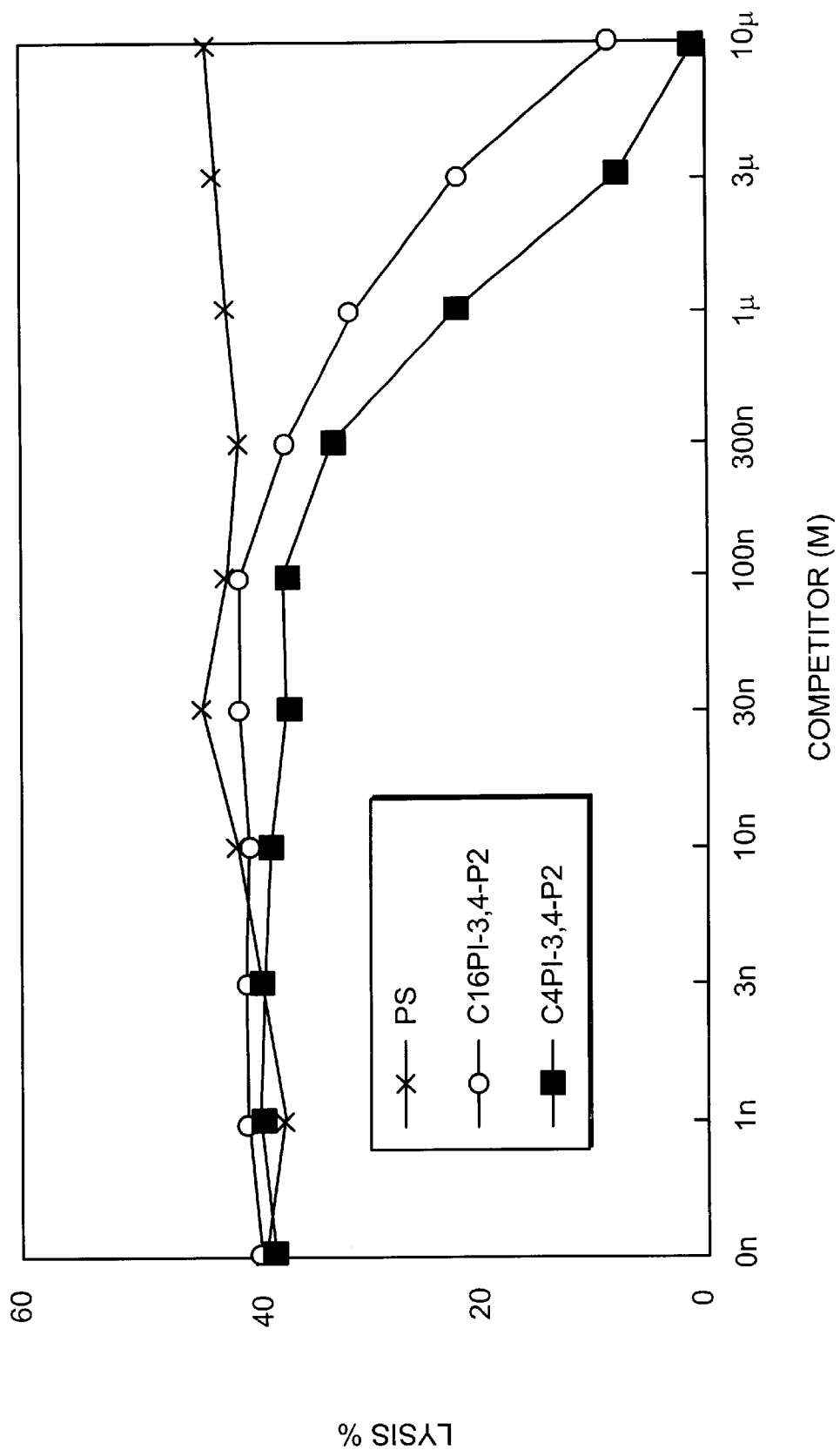
FIG. 5 is a graph showing the reactivity of the antibody 8C2 to PI-3,4-P2 with various length side chains using the competitive reaction in the liposome lysis assay. The ordinate designates the lysis (%) of liposomes, and the abscissa designates the concentrations (M) of the competitive compounds.
Figure 7M:
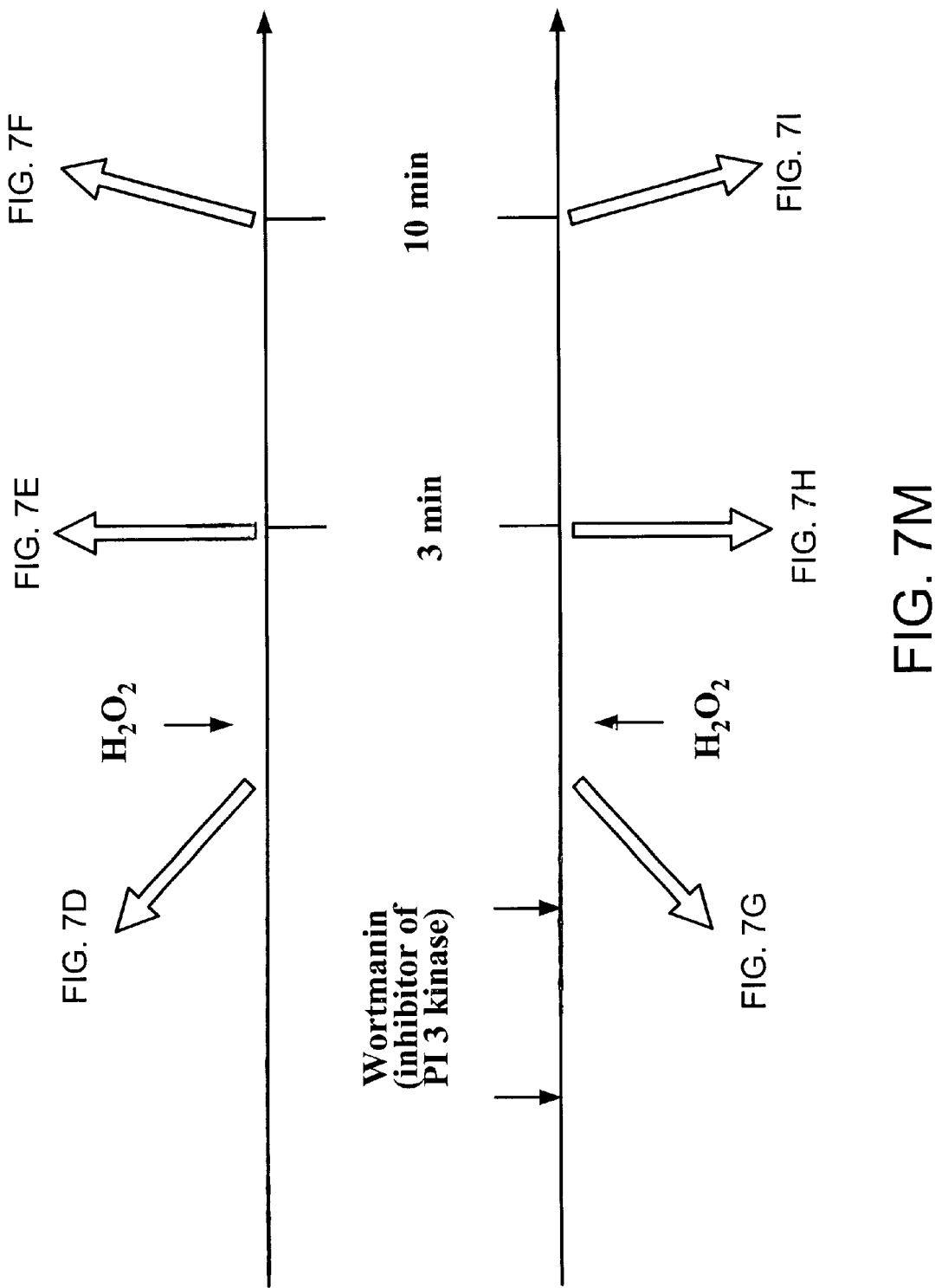
FIG. 7M shows a schematic diagram which further illustrates the subject matter of FIGS. 7A–7L.

As a result, the degree of liposome lysis of PS remained constant in a concentration-independent manner, and the competition with PS was not observed. In contrast, the degree of liposome lysis was reduced as the concentration of C16PI-3,4-P2 or C4PI-3,4-P2 was increased (FIG. 5). This result revealed that the antibody of the present invention recognizes the inositol ring portion independent of the difference of the length of the side chains. The hybridoma 8C2-FNL that produces the antibody of the present invention has been deposited under accession No. FERM BP-6849 at National Institute of Bioscience and Human-Technology Agency of Industrial Science and Technology, of 1–3, Higashi 1-chome, Tsukuba-shi, Ibaraki, 305–8566 Japan since Aug. 18, 1999 (date of original deposition).

EXAMPLE 4

Identification of Hypervariable Regions (CDR) of anti-PI-3.4-P2 Monoclonal Antibody cDNA encoding the variable regions of the monoclonal antibody 8C2 of the present invention that specifically recognizes PI-3,4-P2 was cloned. RNA extracted from the hybridomas was subjected to RT-PCR for amplification of cDNA encoding the variable regions, using signal peptide and constant region sequences as primers. First, the hybridoma 8C2-FNL was incubated in DMEM/10% FCS to prepare poly $A^+$ RNA. Single-stranded cDNA was synthesized from 5 µg of the poly $A^+$ RNA. PCR was performed for 30 cycles, one cycle consisting of 94° C. for 1 minute, 55° C. for 2 minutes and 72° C. for 2 minutes. Restriction enzyme recognition sites corresponding to the cloning sites of pBluescript, which is a cloning vector, are provided at the 5' end of the primer used.

Bands of about 400 bp and about 300 bp were isolated from the amplification products obtained using the heavy chain and light chain, respectively, by agarose gel electrophoresis and independently inserted into the cloning vector pBluescript. After the cloning, the vector was collected. The nucleotide sequence of the insert was confirmed by the dideoxy method using the vector primer and [$\alpha$-$^{32}$P] dATP (F. Sanger, Science, 214, 1205–1210, 1981).

The amino acid sequence the thus obtained gene encodes was deduced, and hypervariable regions CDR were identified by the Chothia Numbering Scheme (http://www.biochem.ucl.ac.uk/~martin/abs/GeneralInfo.html#kabatnum, Al-Lazikani et al., J. Molec. Biol., 273, 927–948, 1997). The results are shown below.

| CDR | Heavy chain | Light chain |
| --- | --- | --- |
| CDR1 | 26–32(5) | 24–39(8) |
| CDR2 | 52–57(6) | 55–61(9) |
| CDR3 | 99–109(7) | 94–102(10) |

EXAMPLE 5

Immunostaining of PI-3,4-P2 Induced by $H_2O_2$ Treatment 293 cells (Japanese Collection of Research Bioresources No. JCRB9068) were cultured on cover slips, to which wortmannin, an inhibitor of PI3 kinase, was added or not added, followed by treatment with 10 mM $H_2O_2$ for 0, 3, or 10 minutes. The cells were fixed in PBS containing 10% formalin at room temperature for 10 minutes, and then reacted in 0.1% Tween 20 at room temperature for 10 minutes to render the cells permeable. The cells were incubated in Dulbecco's medium supplemented with 10% calf serum for 10 min or longer at room temperature for blocking, then reacted with the supernatant from the culture of 8C2-FNL hybridoma as it was in a humidified chamber at room temperature for 2 hours or more, thereby completing the primary reaction (culture medium: Iscove's modified Dulbecco's medium supplemented with 10% fetal bovine serum). Subsequently, FITC-labeled anti-mouse-IgG3 (Southern Biotechnology, 1100–02) was diluted to 1/100 with the blocking buffer and allowed to react with the above reaction mixture for 2 hours or longer at room temperature to complete the secondary reaction. After the reaction, the cells were mounted in 90% glycerol for observation.

As a result, staining for PI-3,4-P2 was observed three and ten minutes after the $H_2O_2$ treatment when wortmannin was not added prior to the induction of PI-3,4-P2 production by $H_2O_2$ treatment, and the staining intensity increased with time. In contrast, no staining of the cells was observed after the $H_2O_2$ treatment when wortmannin was added, confirming that the antibody of the present invention is reactive with PI-3,4-P2 (FIGS. 7A–7L).

To examine the specificity of 8C2, phosphatidylcholine (PC), PI-3,4-P2, or PI-4,5-P2 was added to the culture medium of 293 cells and their effects on the immunoreaction were determined. As a result, PC and PI-4,5-P2 did not compete with PI-3,4-P2, and fluorescence produced by PI-3,4-P2 staining in the cells was observed. In contrast, fluorescence was not observed in the cells to which PI-3,4-P2 was added because the antibody was reacted with P1-3,4-P2 added (FIGS. 8A–8H). These results confirmed that the antibody of the present invention is specific to PI-3,4-P2.

What is claimed is:

1. A monoclonal antibody that specifically recognizes phosphatidylinositol-3,4-bisphosphate, binds to an antigenic determinant that contains an inositol group and a glycerol backbone in said phosphatidylinositol-3,4-bisphosphate, and which is non-cross-reactive or cross-reactive at a level of 1% or less with phosphatidylinositol-4,5-bisphosphate, phosphatidylinositol-3,4,5-triphosphate, phosphatidylinositol-1,4,5-triphosphate, and phosphatidylinositol-1,3,4,5-tetraphosphate.

2. A hybridoma producing the monoclonal antibody of claim 1.

3. The hybridoma of claim 2 wherein the hybridoma is deposited under Accession No. FERM-BP-6849.

4. A kit for immunoassay for phosphatidylinositol-3,4-bisphosphate comprising a monoclonal antibody, or an antigen-binding variable region thereof, that specifically recognizes phosphatidylinositol-3,4-bisphosphate, binds to an antigenic determinant that contains an inositol group and a glycerol backbone in said phosphatidylinositol-3,4-bisphosphate, and which is non-cross-reactive or cross-reactive at a level of 1% or less with phosphatidylinositol-4,5-bisphosphate, phosphatidylinositol-3,4,5-triphosphate, phosphatidylinositol-1,4,5-triphosphate, and phosphatidylinositol-1,3,4,5-tetraphosphate.

5. An isolated immunoglobulin, or the antigen-binding variable region thereof, that specifically recognizes phosphatidylinositol-3,4-bisphosphate, said immunoglobulin, or the variable region thereof, comprising an immunoglobulin heavy chain and immunoglobulin light chain, wherein the immunoglobulin heavy and light chains each comprise complementarity determining regions CDR1, CDR2, and CDR3, further wherein CDR1 comprises an amino acid sequence as set forth in SEQ ID NO:5, CDR2 comprises an amino acid sequence as set forth in SEQ ID NO:6, and CDR3 comprises an amino acid sequence as set forth in SEQ ID NO:7 in the heavy chain, and CDR1 comprises an amino acid sequence as set forth in SEQ ID NO:8, CDR2 comprises an amino acid sequence as set forth in SEQ ID NO:9, and CDR3 comprises an amino acid sequence as set forth in SEQ ID NO:10 in the light chain.

* * * * *